(12) United States Patent
Stawiaski et al.

(10) Patent No.: US 11,291,507 B2
(45) Date of Patent: Apr. 5, 2022

(54) SYSTEM AND METHOD FOR IMAGE BASED REGISTRATION AND CALIBRATION

(71) Applicant: MAKO Surgical Corp., Ft. Lauderdale, FL (US)

(72) Inventors: Jean Stawiaski, Kirchzarten (FR); Fadi Ghanam, Schallstadt (DE); David Hofmann, Freiburg (DE)

(73) Assignee: MAKO Surgical Corp., Ft. Lauderdale, FL (US)

( * ) Notice: Subject to any disclaimer, the term of this patent is extended or adjusted under 35 U.S.C. 154(b) by 121 days.

(21) Appl. No.: 16/441,624

(22) Filed: Jun. 14, 2019

(65) Prior Publication Data

US 2020/0015909 A1    Jan. 16, 2020

Related U.S. Application Data

(60) Provisional application No. 62/698,502, filed on Jul. 16, 2018.

(51) Int. Cl.
*G06T 7/00* (2017.01)
*A61B 34/20* (2016.01)
(Continued)

(52) U.S. Cl.
CPC ............. *A61B 34/20* (2016.02); *A61B 17/16* (2013.01); *A61B 34/10* (2016.02); *A61B 34/30* (2016.02);
(Continued)

(58) Field of Classification Search
CPC ............ A61B 34/20; A61B 2034/2055; A61B 2034/2068; A61B 2090/3983; A61B 2090/371; A61B 2090/363; A61B 2090/3937; A61B 2090/3945; A61B 2090/3995; A61B 5/1127; A61B 6/0492;
(Continued)

(56) References Cited

U.S. PATENT DOCUMENTS 2,017,007 A    10/1935  Liedle
3,891,842 A     6/1975  Strusinski
(Continued)

FOREIGN PATENT DOCUMENTS

DE    1125275 B    3/1962
DE    9306771 U1   7/1993
(Continued)

OTHER PUBLICATIONS

Machine-assisted English translation for DE 1 125 275 extracted from espacenet.com database on Jul. 11, 2019, 8 pages.
(Continued)

*Primary Examiner* — Ian L Lemieux
(74) *Attorney, Agent, or Firm* — Howard & Howard Attorneys PLLC

(57) ABSTRACT

Navigation systems and methods for tracking physical objects near a target site during a surgical procedure are provided, the navigation system comprises a robotic device and an instrument attached to the robotic device; a process of optical registration and calibration can improve operation results by increasing accuracy and speed and eliminate the need for additional reference trackers, such as a pointer.

28 Claims, 7 Drawing Sheets

(51) Int. Cl.
*A61B 34/30* (2016.01)
*A61B 17/16* (2006.01)
*A61B 34/00* (2016.01)
*A61B 34/10* (2016.01)
*G06T 7/73* (2017.01)

(52) U.S. Cl.
CPC .............. *A61B 34/70* (2016.02); *G06T 7/00* (2013.01); *G06T 7/74* (2017.01); *A61B 2017/1602* (2013.01); *A61B 2034/101* (2016.02); *A61B 2034/107* (2016.02); *A61B 2034/2051* (2016.02); *A61B 2034/2063* (2016.02); *A61B 2034/2065* (2016.02); *A61B 2034/2068* (2016.02); *G06K 2209/05* (2013.01)

(58) Field of Classification Search
CPC .............. A61B 90/96; A61B 90/94; G06T 2207/30204; G06T 7/33; G06T 7/74; G06T 19/006; G06T 19/003; G06T 2210/41; G06T 7/00; G06T 7/70; G06K 2209/05; G06K 9/3216
See application file for complete search history.

(56) References Cited

U.S. PATENT DOCUMENTS

| | | |
|---|---|---|
| 5,198,877 A | 3/1993 | Schulz |
| 5,768,443 A | 6/1998 | Michael et al. |
| 5,792,147 A | 8/1998 | Evans et al. |
| 5,954,648 A | 9/1999 | Van Der Brug |
| 5,978,521 A | 11/1999 | Wallack et al. |
| 6,006,126 A | 12/1999 | Cosman |
| 6,137,893 A | 10/2000 | Michael et al. |
| 6,165,181 A | 12/2000 | Heilbrun et al. |
| 6,405,072 B1 | 6/2002 | Cosman |
| 6,497,134 B1 | 12/2002 | Faul et al. |
| 6,529,758 B2 | 3/2003 | Shahidi |
| 6,633,328 B1 | 10/2003 | Byrd et al. |
| 6,675,040 B1 | 1/2004 | Cosman |
| 6,724,922 B1 | 4/2004 | Vilsmeier |
| 6,795,571 B2* | 9/2004 | Kusch .................. A61B 8/00 382/131 |
| 6,915,008 B2 | 7/2005 | Barman et al. |
| 7,224,472 B2 | 5/2007 | Bauch et al. |
| 7,499,806 B2* | 3/2009 | Kermani ............ G01N 21/6428 382/132 |
| 7,561,731 B2 | 7/2009 | Wallace et al. |
| 7,561,733 B2 | 7/2009 | Vilsmeier et al. |
| 7,623,250 B2 | 11/2009 | Moctezuma de la Barrera et al. |
| 7,725,162 B2* | 5/2010 | Malackowski ........ A61B 34/20 600/424 |
| 7,726,564 B2 | 6/2010 | Goldbach |
| 7,728,280 B2 | 6/2010 | Feilkas et al. |
| 7,760,909 B2 | 7/2010 | Manus |
| 7,771,436 B2 | 8/2010 | Moctezuma de la Barrera et al. |
| 8,096,163 B2 | 1/2012 | Goldbach |
| 8,111,904 B2 | 2/2012 | Wallack et al. |
| 8,126,260 B2 | 2/2012 | Wallack et al. |
| 8,300,906 B2 | 10/2012 | Voelker |
| 8,494,614 B2 | 7/2013 | Markowitz et al. |
| 9,008,757 B2* | 4/2015 | Wu ...................... A61B 34/20 600/426 |
| 9,119,655 B2 | 9/2015 | Bowling et al. |
| 9,119,670 B2 | 9/2015 | Yang et al. |
| 9,566,120 B2 | 2/2017 | Malackowski et al. |
| 9,707,043 B2 | 7/2017 | Bozung |
| 9,734,419 B1 | 8/2017 | Ye et al. |
| 9,773,312 B2 | 9/2017 | Lee |
| 10,004,564 B1* | 6/2018 | Beck .................. G06T 7/0012 |
| 2002/0188194 A1 | 12/2002 | Cosman |
| 2003/0040879 A1 | 2/2003 | Jutras et al. |
| 2007/0016008 A1* | 1/2007 | Schoenefeld ......... A61B 90/36 600/424 |
| 2007/0173790 A1 | 7/2007 | Moctezuma De La Barrera et al. |
| 2007/0253541 A1 | 11/2007 | Sukovic et al. |
| 2008/0004633 A1 | 1/2008 | Arata et al. |
| 2008/0107305 A1 | 5/2008 | Vanderkooy et al. |
| 2009/0163930 A1 | 6/2009 | Aoude et al. |
| 2011/0025853 A1* | 2/2011 | Richardson ............ H04N 5/247 348/159 |
| 2011/0054449 A1 | 3/2011 | Tien et al. |
| 2011/0157373 A1 | 6/2011 | Ye et al. |
| 2014/0125771 A1* | 5/2014 | Grossmann ............ G06T 5/006 348/47 |
| 2014/0200621 A1 | 7/2014 | Malackowski et al. |
| 2014/0232832 A1 | 8/2014 | Sander |
| 2014/0276943 A1* | 9/2014 | Bowling ................ A61B 90/03 606/130 |
| 2014/0375822 A1 | 12/2014 | Jain et al. |
| 2015/0110347 A1* | 4/2015 | Suzuki ................. G06K 9/2081 382/103 |
| 2015/0223725 A1 | 8/2015 | Engel et al. |
| 2016/0125592 A1* | 5/2016 | Becker ...................... G06T 7/73 348/90 |
| 2016/0125594 A1* | 5/2016 | Becker ..................... B23K 9/32 348/90 |
| 2016/0166335 A1 | 6/2016 | Roger et al. |
| 2016/0191887 A1 | 6/2016 | Casas |
| 2017/0007150 A1 | 1/2017 | Jeon et al. |
| 2017/0026560 A1* | 1/2017 | Whitehouse ......... H04N 5/2352 |
| 2017/0071508 A1 | 3/2017 | Kaiser et al. |
| 2017/0165008 A1* | 6/2017 | Finley ..................... A61B 6/547 |
| 2017/0281283 A1 | 10/2017 | Siegler et al. |
| 2018/0125586 A1 | 5/2018 | Sela et al. |
| 2018/0200001 A1* | 7/2018 | Erbe ...................... A61B 34/20 |
| 2019/0000564 A1* | 1/2019 | Navab ..................... G06T 7/521 |
| 2019/0320995 A1* | 10/2019 | Amiri ..................... A61B 6/463 |
| 2019/0328464 A1* | 10/2019 | Saur ..................... G02B 21/365 |

FOREIGN PATENT DOCUMENTS

| | | |
|---|---|---|
| DE | 19639615 A1 | 4/1998 |
| DE | 10225077 A1 | 12/2003 |
| DE | 10246147 A1 | 4/2004 |
| DE | 10323091 A1 | 12/2004 |
| DE | 202004014857 U1 | 4/2005 |
| DE | 202007007054 U1 | 7/2007 |
| DE | 202007016962 U1 | 4/2008 |
| DE | 102008023330 A1 | 11/2009 |
| DE | 102008057820 A1 | 5/2010 |
| DE | 102011054730 A1 | 4/2013 |
| DE | 102012220116 A1 | 1/2014 |
| DE | 102013202575 A1 | 8/2014 |
| DE | 102017105158 A1 | 9/2018 |
| EP | 0672389 A2 | 9/1995 |
| EP | 1340470 A1 | 9/2003 |
| EP | 1933276 A1 | 6/2008 |
| EP | 3025665 A1 | 6/2016 |
| WO | 199611624 A2 | 4/1996 |
| WO | 2007115825 A1 | 10/2007 |
| WO | 2017121926 A1 | 7/2017 |

OTHER PUBLICATIONS

Machine-assisted English translation for DE 93 06 771 extracted from espacenet.com database on Jul. 11, 2019, 9 pages.
English language abstract and machine-assisted English translation for DE 196 39 615 extracted from espacenet.com database on Jul. 11, 2019, 25 pages.
English language abstract and machine-assisted English translation for DE 102 25 077 extracted from espacenet.com database on Jul. 11, 2019, 18 pages.
English language abstract and machine-assisted English translation for DE 102 46 147 extracted from espacenet.com database on Jul. 11, 2019, 12 pages.
English language abstract and machine-assisted English translation for DE 103 23 091 extracted from espacenet.com database on Jul. 11, 2019, 18 pages.

(56) References Cited

OTHER PUBLICATIONS

English language abstract and machine-assisted English translation for DE 20 2004 014 857 extracted from espacenet.com database on Jul. 11, 2019, 9 pages.
English language abstract for DE 20 2007 007 054 extracted from espacenet.com database on Jul. 11, 2019, 1 page.
Machine-assisted English translation for DE 20 2007 016 962 extracted from espacenet.com database on Jul. 11, 2019, 7 pages.
English language abstract and machine-assisted English translation for DE 10 2008 023 330 extracted from espacenet.com database on Jul. 11, 2019, 12 pages.
English language abstract and machine-assisted English translation for DE 10 2008 057 820 extracted from espacenet.com database on Jul. 11, 2019, 8 pages.
English language abstract and machine-assisted English translation for DE 10 2011 054 730 extracted from espacenet.com database on Jul. 11, 2019, 16 pages.
English language abstract for DE 10 2013 202 575 extracted from espacenet.com database on Jul. 11, 2019, 1 page.
English language abstract for EP 1 340 470 extracted from espacenet.com database on Jul. 11, 2019, 1 page.
English language abstract for EP 1 933 276 extracted from espacenet.com database on Jul. 11, 2019, 1 page.
Belongie, S. et al., "Matching Shapes", The 8th International Conference on Computer Vision, Vancouver, Canada, 2001, pp. 454-461.
Abstract of Brown, M.Z. et al., "Advances in Computational Stereo", IEEE Transactions on Pattern Analysis and Machine Intelligence, vol. 25, No. 8, Aug. 2003, pp. 993-1008, 2 pages.
Duda, R.O. et al., "Use of the Hough Transformation to Detect Lines and Curves in Pictures", Communications of the ACM, Association for Computing Machinery, vol. 15, Jan. 1972, pp. 11-15.
Hartley, R. et al., Multi View Geometry in Computer Vision, Second Edition, Cambridge University Press, 2000, p. 312.
Hartley, R.I., "Theory and Practice of Projective Rectification", International Journal of Computer Vision, vol. 35, No. 2, 1999, pp. 115-127.
Hirschmuller, H., "Stereo Processing by Semiglobal Matching and Mutual Information", IEEE Transactons on Pattern Analysis and Machine Intelligence, vol. 30, No. 2, Feb. 2008, pp. 328-341.
Horn, B.K.P., "Closed-Form Solution of Absolute Orientation Using Unit Quaternions", Journal of the Optical Society of America, vol. 4, No. 4, Apr. 1987, pp. 629-642.
Abstract of Huang, K.S. et al., "Least-squares fitting of two 3-D point sets", IEEE Trans Pattern Anal Machine Intell., vol. 9, 1987, pp. 698-700, 1 page.
Kanatani, K., "Analysis of 3-D rotation fitting", IEEE Trans Pattern Anal Machine Intell., vol. 16, 1994, pp. 543-549.
Scharstein, D. et al., "A Taxonomy and Evaluation of Dense Two-Frame Stereo Correspondence Algorithms", International Journal of Computer Vision, vol. 47, Apr. 2002, pp. 1-3 and 7-42.
Umeyama, S., "Least-squares estimation of transformation parameters between two point patterns", IEEE Trans Pattern Anal Machine Intell., vol. 13, 1991, pp. 376-380.
Machine-assisted English language abstract for DE 10 2012 220 116 A1 extracted from espacenet.com database on Feb. 2, 2022, 2 pages.
Machine-assisted English language abstract and machine-assisted English translation for DE 10 2017 105 158 A1 extracted from espacenet.com database on Feb. 2, 2022, 22 pages.

* cited by examiner

SYSTEM AND METHOD FOR IMAGE BASED REGISTRATION AND CALIBRATION

RELATED APPLICATIONS

This application claims priority to and all advantages of U.S. Provisional Patent Application No. 62/698,502, filed on Jul. 16, 2018, the content of which is incorporated herein by reference.

TECHNICAL FIELD

The present disclosure relates generally to a system and method for image based registration and calibration useful in surgical navigation.

BACKGROUND

Navigation systems assist users in precisely locating objects. For instance, navigation systems are used in industrial, aerospace, and medical applications. In the medical field, navigation systems assist surgeons in precisely placing surgical instruments relative to a target site in a patient, for example, during a surgical operation. The target site usually requires some form of treatment, such as tissue removal. Conventional navigation systems employ a localizer including one or more sensors that cooperate with trackers to provide position and/or orientation data associated with the surgical instrument and the target site, e.g., the volume of bone to be removed. These trackers allow a surgeon to see the position and/or orientation of the surgical tool overlaid on a monitor in conjunction with a preoperative or an intraoperative image of the patient. The preoperative images may be generated by MRI, CT scans, or other well-known medical imaging technologies, prior to beginning the surgical operation.

The localizer is usually placed so that it has a field of view of the trackers, that is, the localizer is positioned so that the target site of the patient is within the target space of the localizer. The trackers include identifiable arrays of fiducials that are fixed to a surgical instrument and/or to a patient to move in concert with the surgical instrument or the patient, respectively. From the detected position of the trackers, the surgical navigation system can determine the position and/or orientation of the surgical tool or patient anatomy, and monitor and track the position and/or orientation for changes over time. The term position refers to the three-dimensional coordinate values of an object's coordinate system relative to a reference coordinate system used by the surgical navigation system. The term orientation refers to the pitch, roll and yaw of the object's coordinate system relative to the reference coordinate system. Collectively, the position and the particular pitch, roll, and yaw values of a given orientation may be referred to as the object's pose in the reference coordinate system. When both the position and orientation (or pose) are defined, the object is known to and trackable by the surgical navigation system.

The tracker attached to the patient is often rigidly secured to the bone being treated, thereby maintaining a fixed relationship with respect to the target site owing to the rigid nature of the bone, the rigid structure of the tracker and the fixed securement therebetween. By using separate trackers on the surgical instrument and the patient, the treatment end of the surgical instrument can be precisely positioned at the target site by the surgeon aided by the navigation system.

During an initial phase of the operation, an object, whether a surgical tool or a patient's anatomy, must be calibrated or registered to the surgical navigation system. The process of calibration, or registration, refers to establishing a relationship between a physical object and its tracker to virtual representations of the object and tracker as data within the surgical navigation system, that is, as virtual object data and virtual tracker data, respectively. The virtual data, whether for the object or the tracker, may or may not be a model of the object. Rather the virtual data may comprise information sufficient to identify or designate certain points of interest, and may further include other information about the dimensional characteristics of the object. The virtual data may be established pre-operatively, based on pre-existing modeling or object specification data, or may be established intra-operatively, based on imaging the object in situ. For example, preoperative imaging of a patient's anatomy may be used to generate a 3D model of that anatomy as virtual object data in the memory and virtual environment of the surgical navigation system. Likewise, a surgical tool may be manufactured according to known geometry and structure. This geometry and structure may be represented in a 3D model of that tool as virtual object data in the memory and virtual environment of the surgical navigation system. To perform the calibration, additional reference pointers or frames having additional tracker fiducial arrays may be required to touch off reference points according to a registration sequence.

The localizer is typically provided with multiple sensing technologies variously adapted for beneficial use in a particular aspect of the operation. In one example, a localizer may be provided with sensors adapted for navigation. The sensor(s) configured for navigation are adapted to cycle at a high frequency to track accurately small movements over small increments of time. In order to achieve the high frequency cycling, the navigation sensors may disadvantageously be limited in spectrum, resolution and/or range to minimize data processing requirements.

The localizer may be further provided with sensors adapted for machine vision or other applications beneficial to the operation. For example, the localizer may be provided with one or more optical cameras to provide video recording of the surgical operation. Considering the different functions various sensors may be applied to perform and/or the post-processing performed on the sensor data, the localizer may thus include multiple sets of discrete sensors. Moreover, conventional surgical navigation systems may require multiple sensors and pointers to perform initial calibrations due to the need to relate different aspects of the object and the tracker.

Thus, there is a need in the art for systems and methods that address the calibration, identification and tracking of physical objects during surgery.

SUMMARY

In a first embodiment, a method of locating a physical object in a target space is provided. The physical object to be located has a geometry represented by virtual object data. A tracker is coupled to the physical object for movement with the object. The tracker includes a marker array that has an arrangement defined by virtual tracker data. The method according to the first embodiment includes capturing one or more first exposure images of the target space containing the physical object and the tracker at a first exposure with a first of at least one camera. The method includes capturing one or more second exposure images of the target space containing the physical object and the tracker at a second exposure with the first of the at least one camera, where the second exposure is different from the first exposure. The method includes estimating a tracker pose based on the one or more first exposure images by relating the one or more first exposure images with the virtual tracker data defining the marker arrangement. The method also includes correlating the virtual object data to the estimated tracker pose by recognizing the physical object in the one or more second exposure images based on the virtual object data.

In accordance with the present disclosure, the method of the first embodiment, in one example, also includes capturing one or more first exposure images of the target space with a second of the at least one camera. The method of the first embodiment may also include capturing one or more second exposure images of the target space with a second of the at least one camera. In one aspect, the first exposure may be shorter in time than the second exposure. In one aspect, the first exposure may be lower in illumination than the second exposure. In one aspect, the first and the second of the at least one camera is an infrared imaging device, and the method of the first embodiment includes the step of emitting infrared light onto the target space with an infrared emitter.

In the method of the first embodiment, in one example, the first of the at least one camera and the second of the at least one camera are rigidly mounted to a common support structure and separated by a separation distance. The separation distance is selected from among greater than six inches, greater than eight inches, greater than twelve inches, or greater than twenty-four inches.

In the method of the first embodiment, in one example, the first exposure has a duration in the range of 100 to 500 microseconds. For instance, the first exposure has a duration of about 300 microseconds. In one example, the first exposure has a first duration and the second exposure has a second duration, and the second duration is at least 10 times the length of the first duration. In one example, the second exposure has a duration in the range of 10 to 50 milliseconds. In one example, the second exposure has a duration of about 30 milliseconds.

In the method of the first embodiment, in one example, the step of capturing the one or more second exposure images commences within an interval of less than 300 microseconds following the conclusion of the step of capturing the first exposure images at the first exposure.

In one example of the method of the first embodiment, the physical object is a patient's anatomy, and the method includes the steps of capturing preoperative images of the patient's anatomy; and generating virtual object data from the preoperative images.

In one example of the method of the first embodiment, the physical object is a surgical tool, and the method includes the steps of querying a database of surgical tool models; and retrieving virtual object data based on querying the database of surgical tool models.

In one example of the method of the first embodiment includes the step of querying a database of virtual tracker data.

In another embodiment, a system for locating a physical object in a target space is provided. The physical object has a geometry represented by virtual object data. A tracker is coupled to the physical object for movement with the object. The tracker has a marker array and the marker array has a marker arrangement defined by virtual tracker data. The system includes a first camera operable to capture first exposure images of the virtual space at a first exposure and second exposure images of the virtual space at a second exposure. The system includes a control and processing subsystem in electronic communication with the first camera. The control and processing system includes a memory device operable to store virtual object data, and virtual tracker data. The control and processing system includes instructions that when executed cause the system to capture one or more first exposure images of the target space containing the physical object and the tracker at the first exposure with the first camera. The instructions also cause the system to capture one or more second exposure images of the target space containing the physical object and the tracker at the second exposure with the first camera. The instructions also cause the system to estimate a tracker pose based on the one or more first exposure images by relating the one or more first exposure images with the virtual tracker data defining the marker arrangement. The instructions also cause the system to correlate the virtual object data to the estimated tracker pose by recognizing the physical object in the one or more second exposure images based on the virtual object data.

BRIEF DESCRIPTION OF THE DRAWINGS

Advantages of the present disclosure will be readily appreciated as the same becomes better understood with reference to the following detailed description when considered in connection with the accompanying drawings.

DETAILED DESCRIPTION

Figure 1:
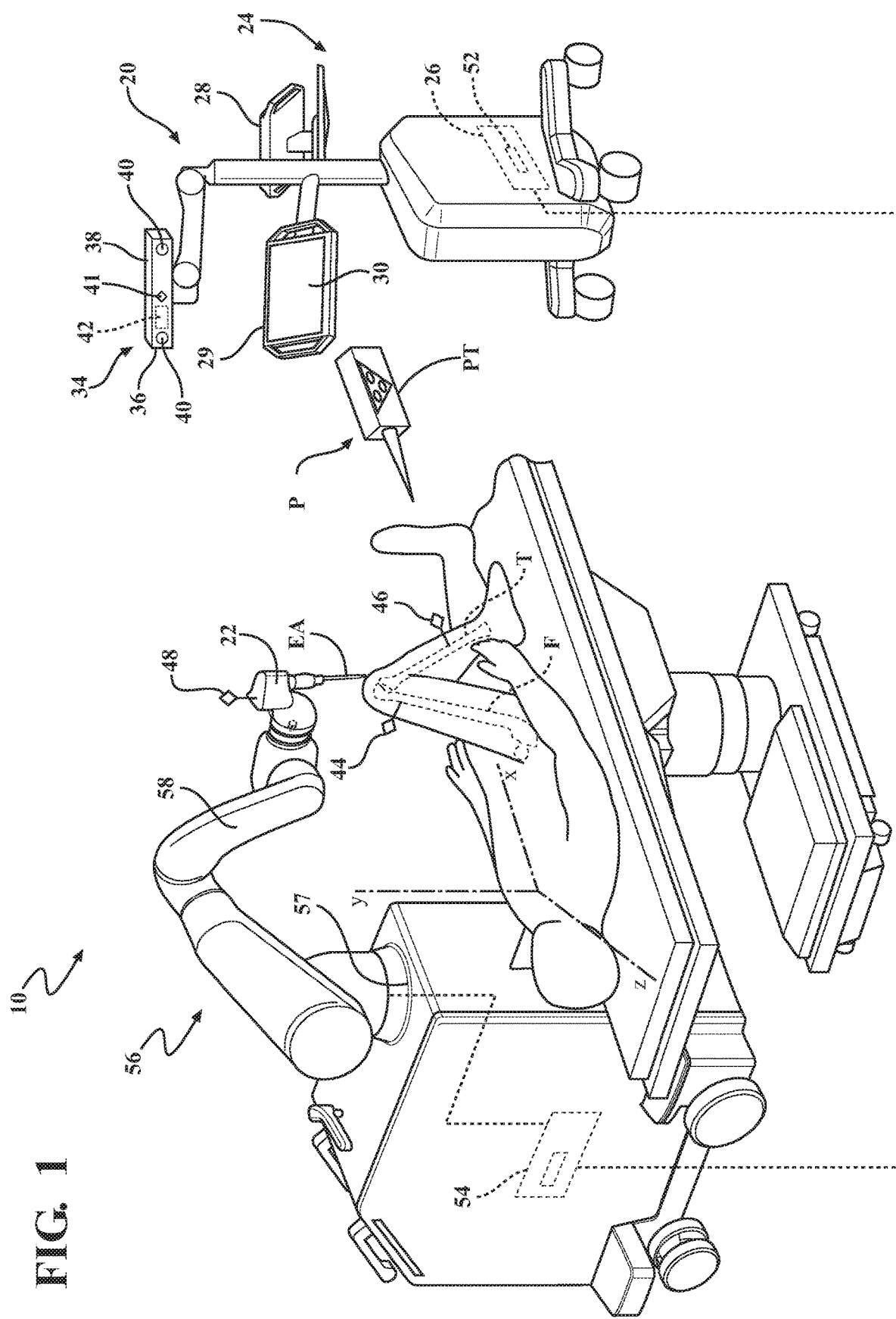
FIG. 1 is a perspective view of a surgical navigation system being used in conjunction with a robotic surgical device.

Referring to FIG. 1, a surgical system 10 is illustrated for performing surgery on a patient. The version shown in FIG. 1 includes a surgical navigation system 20. The surgical navigation system 20 is shown in a surgical setting such as an operating room of a medical facility. The surgical navigation system 20 is set up to track movement of various objects in the operating room. Such objects include, for example, a surgical instrument 22, a femur F of the patient, a tibia T of the patient, and/or a robotic manipulator 56. The surgical navigation system 20 tracks these objects for purposes of displaying their relative positions and orientations to the surgeon and, in some cases, for purposes of controlling or constraining movement of the surgical instrument 22 or and/or robotic manipulator 56 relative to virtual cutting boundaries associated, in the illustrated example, with the femur F and tibia T.

The surgical navigation system 20 includes a computer cart assembly 24 that houses a navigation computer 26. A navigation interface is in operative communication with the navigation computer 26. The navigation interface includes a first display 28 adapted to be situated outside of the sterile field and a second display 29 adapted to be situated inside the sterile field. The displays 28, 29 are adjustably mounted to the computer cart assembly 24. First and second input devices (not shown) such as a keyboard and mouse can be used to input information into the navigation computer 26 or otherwise select/control certain aspects of the navigation computer 26. Other input devices are contemplated including a touch screen 30, gesture control, or voice-activation.

A localizer 34 communicates with the navigation computer 26. In the embodiment shown, the localizer 34 is an optical localizer and includes a camera unit 36. The camera unit 36 has an outer casing 38 that houses one or more optical sensors 40. The optical sensors 40 may be rigidly mounted to a common support structure. The outer casing 38 may provide the common support structure for the optical sensors 40. Alternatively, a rigid support structure common to the optical sensors 40 may be encased by, but distinct from, the outer casing 38. As illustrated in FIG. 1, the optical sensors 40 are disposed at opposite ends of the elongated camera unit 36, such that the optical sensors are arranged stereoscopically and separated by a separation distance. Representative separation distances may be greater than about 6 inches, greater than about 8 inches, greater than about 12 inches, or greater than about 24 inches. Larger separation distances may improve the three-dimensional depth perception of the system at the cost of larger component size. The larger the size of the camera unit 36 may increase the difficulty of arranging the camera unit 36 to maintain an obstruction-free view of the target space. In some embodiments at least two optical sensors 40 are employed. The optical sensors 40 are capable of variable attenuation of radiant energy, for example, light, into signals as small bursts of electrical current that convey information. The camera unit 36 may also include a video camera 41 or other additional sensing devices. The video camera 41 may include similar or different optical sensing technology as those employed in the optical sensors 40. For example, the optical sensors 40 may be adapted to sense light in the infrared or near-infrared spectrum, while the video camera 41 may be adapted to sense light in the visible spectrum.

The optical sensors 40 may be separate charge-coupled devices (CCD). In some embodiments, two, two-dimensional CCDs are employed. In some cases, the optical sensors 40 are arranged for stereoscopic operation, or single cameras combined with depth sensors, laser range finders, and the like, may be used. It should be appreciated that in other embodiments, separate camera units, each with a separate CCD, or two or more CCDs, could also be arranged around the operating room. The optical sensors 40 may include CCDs capable of detecting infrared (IR) radiant energy. In alternative embodiments, the optical sensors may employ other sensing technology, including, but not limited to, complimentary metal-oxide semiconductor (CMOS) active-pixel sensors, and the like.

The camera unit 36 may be mounted on an adjustable arm or other articulated support structure of the cart assembly 24 to selectively position the localizer 34 with a, preferably unobstructed, field of view of the target space including the surgical setting within which will be the patient anatomy and trackers, as discussed below. In some embodiments, the camera unit 36 is adjustable in at least one degree of freedom by rotating about a rotational joint. In other embodiments, the camera unit 36 is adjustable about two or more degrees of freedom.

The camera unit 36 includes a camera controller 42 in communication with the optical sensors 40 to receive signals from the optical sensors 40. The camera controller 42 communicates with the navigation computer 26 through either a wired or wireless connection (not shown). One such connection may be an IEEE 1394 interface, which is a serial bus interface standard for high-speed communications and isochronous real-time data transfer. Other suitable connections types may include Ethernet, thunderbolt, USB interface, PCI Express, DisplayPort, or the like. The connection could also use a company specific protocol. In other embodiments, the optical sensors 40 may communicate directly with the navigation computer 26, such that the navigation computer incorporates the functionality of, and thus operates as, the camera controller 42. Processing of the signals from the optical sensors 40 may occur at the camera controller 42. Alternatively, the camera controller 42 may communicate the signals to the navigation computer 26 for processing.

The navigation computer 26 can be a personal computer or laptop computer. Navigation computer 26 has the displays 28, 29, central processing unit (CPU) and/or other processors, memory (not shown), and storage (not shown). The navigation computer 26 is loaded with software as described below. The software converts the signals received from the camera unit 36 or the optical sensors 40 into data representative of the position and orientation of the objects being tracked. Position and orientation signals and/or data is used by the navigation computer 26 for purposes of tracking objects. The computer cart assembly 24, display 28, and camera unit 36 may be like those described in U.S. Pat. No. 7,725,162 to Malackowski, et al. issued on May 25, 2010, entitled "Surgery System," hereby incorporated by reference.

The surgical system 10 illustrated in FIG. 1 includes a plurality of tracking devices 44, 46, 48, also referred to herein simply as trackers. In the illustrated embodiment, one tracker 44 is coupled to the femur F of the patient and another tracker 46 is coupled to the tibia T of the patient. Trackers 44, 46 may be attached to the femur F and tibia T in the manner shown in U.S. Pat. No. 7,725,162 to Malackowski, et al. issued on May 25, 2010, entitled "Surgery System," hereby incorporated by reference. Trackers 44, 46 could also be mounted like those shown in U.S. Pat. No. 9,566,120 to Malackowski, et al. issued Feb. 14, 2017, entitled, "Navigation Systems and Methods for Indicating and Reducing Line-of-Sight Errors," the disclosure of which is hereby incorporated by reference. In alternative embodiments, a tracker (not shown) is attached to the patella to track a position and orientation of the patella. In other embodiments, trackers may be mounted to other tissue types or parts of the anatomy according to the needs of a particular operation.

An instrument tracker 48 is coupled to the surgical instrument 22. The instrument tracker 48 may be integrated into the surgical instrument 22 during manufacture or may be separately mounted to the surgical instrument 22 in preparation for the surgical procedure. The working end of the surgical instrument 22, which is being tracked by virtue of the instrument tracker 48, may be an energy applicator EA such as a rotating bur, saw blade, electrical ablation device, or the like. The energy applicator EA may be a separate component such as a replaceable bur, saw blade, ablator, or the like that is releasably connected to a handpiece of the surgical tool 22 or the energy application EA may be integrally formed with the handpiece.

The trackers 44, 46, 48 may be active trackers or passive trackers. Active trackers require a power source and have an array of fiducials (also referred to as tracking elements or markers) that actively generate and emit radiation in a wavelength detectable by the optical sensors 40. The fiducials of an active tracker may be a light emitting diode (LED), including, for example, an infrared LED. The array of active fiducials may be "always on" or may be operative to selectively fire, that is emit radiation, according to and in response to commands from the surgical navigation system 20. In such selective-fire active trackers, the tracker may communicate by way of a wired or a wireless connection with the navigation computer 26 of surgical navigation system 20. In alternative embodiments, the tracker may include passive trackers. That is, the array of passive trackers focus or reflect ambient radiation or radiation that has been emitted into the target space, for example by one or more infrared LEDs provided on the camera unit 36 or elsewhere associated with the surgical system 10. The active tracker may be battery powered with an internal battery or may have leads to receive power through the navigation computer 26, which, like the camera unit 36, may receive external power. The passive tracker array typically does not require a power source.

In the embodiment shown, the surgical instrument 22 is attached to a surgical manipulator 56. Such an arrangement is shown in U.S. Pat. No. 9,119,655 to Bowling et al, issued Sep. 1, 2015, entitled, "Surgical Manipulator Capable of Controlling a Surgical Instrument in Multiple Modes," the disclosure of which is hereby incorporated by reference.

In other embodiments, the surgical instrument 22 may be manually positioned by only the hand of the user, without the aid of any cutting guide, jig, or other constraining mechanism such as a manipulator or robot. Such a surgical instrument is described in U.S. Pat. No. 9,707,043 to Bozung et al., issued Jul. 18, 2017, the disclosure of which is hereby incorporated by reference.

The optical sensors 40 of the localizer 34 receive signals from the trackers 44, 46, 48. In the illustrated embodiment, the trackers 44, 46, 48 are active trackers. In this embodiment, each tracker 44, 46, 48 has at least three always-on active tracking elements or markers for transmitting light signals, such as infrared light, to the optical sensors 40.

Initially, the objects to be located are viewed by the optical sensors 40 and identified. The objects may be identified by selecting the objects to be tracked using an input device connected to the navigation computer 26. The navigation computer 26 may store detailed information regarding numerous objects in memory or data storage on the navigation computer 26 and the user may be able to manually select the objects to be tracked from a database of objects.

Additionally, or alternatively, the navigation computer 26 may identify the objects to be tracked based on a pre-operative surgical plan. In this case, the navigation computer 26 may have a preset list of workflow objects that may be used in the pre-scripted surgical workflow. The navigation computer 26 may actively search for and locate the workflow objects using software. For instance, groups of pixels associated with different sizes and shapes of the various objects may be stored in the navigation computer 26. By selecting/identifying the objects to be located/tracked, the software identifies the corresponding group of pixels and the software then operates to detect like groups of pixels using conventional pattern recognition technology.

Additionally, or alternatively, the objects to be located/tracked can be identified using an interface in which one of the participants outlines or selects the objects to be tracked on one or more of the displays 28, 29. For instance, images taken by the optical sensors 40, or video camera 41, of the surgical site may be displayed on one or more of the displays 28, 29 (and/or other displays). The participant then, using a mouse, digital pen, or the like, traces objects to be located/tracked on the display 28 and/or 29. The software stores the pixels associated with the object that was traced into its memory. The participant (or other user) may identify each object by a unique identifier such as naming the object using the software so that the saved group of pixels may be associated with the unique identifier. Multiple objects could be stored in this manner. The navigation computer 26 utilizes conventional pattern recognition and associated software to later detect these objects. The navigation system 20 is able to detect movement of these objects by continuously taking images, reviewing the images, and detecting movement of the groups of pixels associated with the objects.

In conventional surgical navigation systems, the objects to be tracked are initially located and registered using a navigation pointer P. For example, the navigation pointer P may have an integrated tracker PT. The navigation computer 26 may store initial data corresponding to a location of the tip of the pointer P relative to the tracker PT such that the navigation system 20 is able to locate and track the tip of the pointer P in the localizer coordinate system LCLZ. Accordingly, prior to the start of the surgical procedure, once all the objects are located in their desired locations, one of the participants may touch all of the objects with the pointer P, while identifying the objects in the navigation system 20 using one of the input devices described above. So, for example, when the participant touches the surgical instrument 22 with the tip of the pointer P, the participant may simultaneously trigger collection of that point in the localizer coordinate system LCLZ (via another input device, such as a foot pedal). When the point is collected, the participant can also enter into the navigation software the identity of the object (via typing, pull-down selection from a list of objects, etc.). The use of the navigation pointer during calibration or registration is time-consuming and requires precision by the surgeon in order to locate and identify objects to the navigation system 20.

Figure 2:
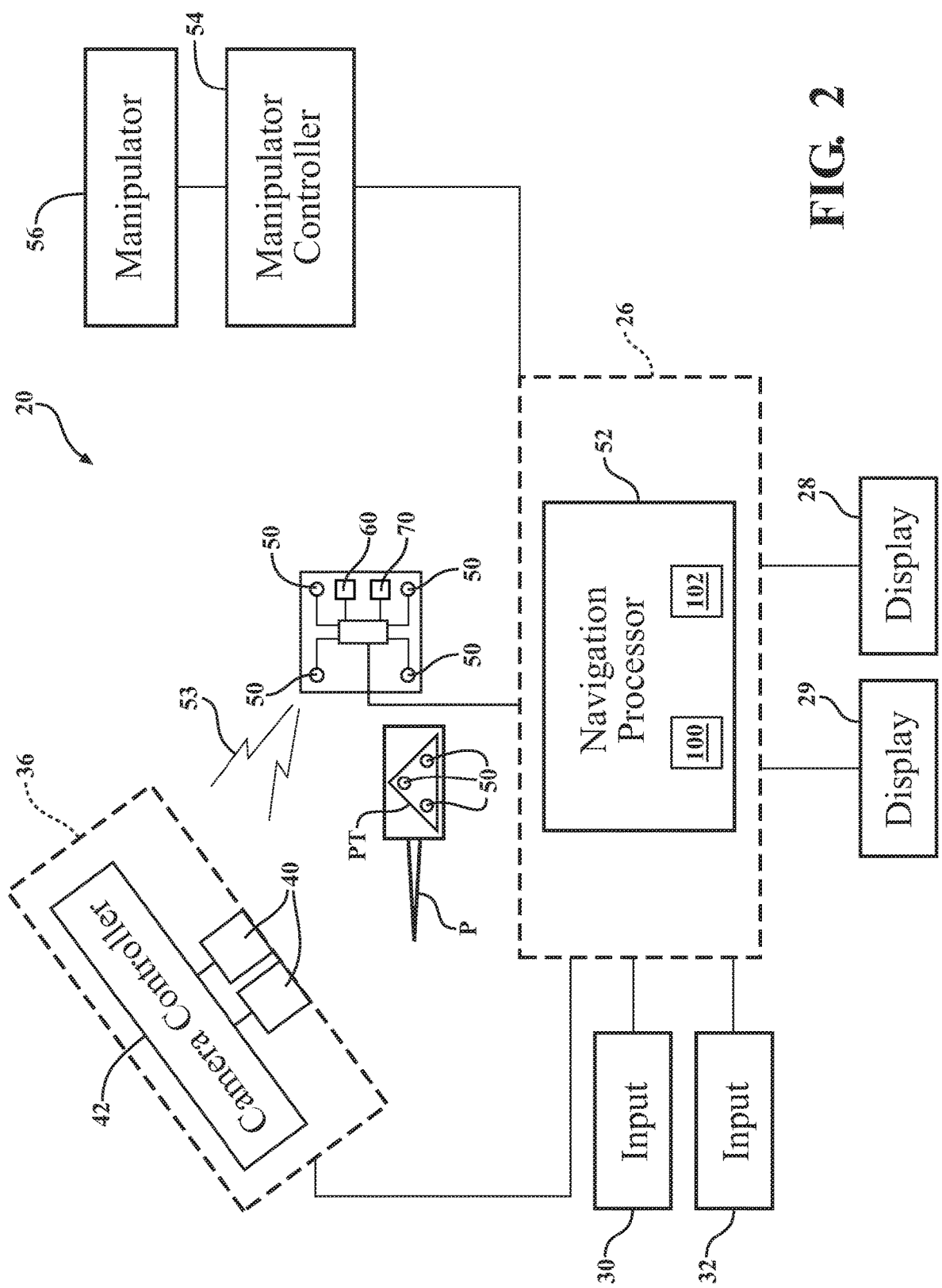
FIG. 2 is a schematic view of a control system for controlling the surgical navigation system and robotic surgical device.

Referring to FIG. 2, a schematic view of a control system for controlling the surgical navigation system 20 and robotic surgical device 56 is shown. In this schematic, each of the LEDs 50 are illustrated connected to a tracker controller 62 located in a housing (not shown) of the associated tracker 44, 46, 48 that transmits/receives data to/from the navigation computer 26. In one embodiment, the tracker controllers 62 transmit data through wired connections with the navigation computer 26. In other embodiments, a wireless connection may be used. In these embodiments, the navigation computer 26 has a transceiver (not shown) to receive the data from the tracker controller 62. In other embodiments, the trackers 44, 46, 48 may have passive markers (not shown), such as reflectors that reflect light, for example, light emitted by an LED provided on camera unit 36. For example, the camera unit 36 may include complementary emitters in a wavelength to which the optical sensors 40 are sensitive. The reflected light is then received by the optical sensors 40. In some embodiments, the trackers 44, 46, 48 may also include a gyroscope sensor 60 and accelerometer 70, such as the trackers shown in U.S. Pat. No. 9,008,757 to Wu, et al., issued on Apr. 14, 2015, entitled, "Navigation System Including Optical and Non-Optical Sensors," the entire disclosure of which is hereby incorporated by reference. These additional sensors 60, 70, may provide information to the navigation computer 26 for use by the navigation computer to determine or track the trackers' 44, 46, 48 position or orientation.

The navigation computer 26 includes a navigation processor 52. It should be understood that the navigation processor 52 could include one or more processors to control operation of the navigation computer 26. The processors can be any type of microprocessor or multi-processor system. The term "processor" is not intended to limit the scope of the invention to a single processor.

As illustrated in FIG. 2, the camera unit 36 receives optical signals 53 from the LEDs 50 of the trackers 44, 46, 48 and outputs to the processor 52 signals relating to the position of the LEDs 50 of the trackers 44, 46, 48 relative to the localizer 34. Based on the received optical (and non-optical signals in some embodiments), navigation processor 52 generates data indicating the relative positions and orientations of the trackers 44, 46, 48 relative to the localizer 34.

Prior to the start of the surgical procedure, additional data are loaded into the navigation processor 52. Based on the position and orientation of the trackers 44, 46, 48 and the previously loaded data, such as virtual object data representing the geometry of the object to which the tracker is attached, navigation processor 52 determines the position of the working end of the surgical instrument 22 (e.g., the centroid of a surgical bur) and the orientation of the surgical instrument 22 relative to the tissue against which the working end is to be applied. In some embodiments, navigation processor 52 forwards these data to a manipulator controller 54. The manipulator controller 54 can then use the data to control a robotic manipulator 56 as described in U.S. Pat. No. 9,119,655 to Bowling, et al., incorporated above.

The navigation processor 52 also generates image signals that indicate the relative position of the surgical instrument working end to the tissue. These image signals are applied to the displays 28, 29. Displays 28, 29, based on these signals, generate images that allow the surgeon and staff to view the relative position of the surgical instrument working end to the surgical site. The displays, 28, 29, as discussed above, may include a touch screen 30 or other input/output device that allows entry of commands.

In the embodiment shown in FIG. 1, the surgical tool 22 forms part of an end effector of the manipulator 56. The manipulator 56 has a base 57, a plurality of links 58 extending from the base 57, and a plurality of active joints (not numbered) for moving the surgical tool 22 with respect to the base 57. The links 58 may form a serial arm structure as shown in FIG. 1, a parallel arm structure (shown for example in FIG. 3), or other suitable structure. The manipulator 56 has the ability to operate in a manual mode in which a user grasps the end effector of the manipulator 56 in order to cause movement of the surgical tool 22 (e.g., directly, through force/torque sensor measurements that cause active driving of the manipulator 56, or otherwise) or a semi-autonomous mode in which the surgical tool 22 is moved by the manipulator 56 along a predefined tool path (e.g., the active joints of the manipulator 56 are operated to move the surgical tool 22 without requiring force/torque on the end effector from the user). An example of operation in a semi-autonomous mode is described in U.S. Pat. No. 9,119,655 to Bowling, et al., incorporated above. A separate tracker (not shown) may be attached to the base 57 of the manipulator 56 to track movement of the base 57.

The manipulator controller 54 may have a central processing unit (CPU) and/or other manipulator processors, memory (not shown), and storage (not shown). The manipulator controller 54, also referred to as a manipulator computer, is loaded with software as described below. The manipulator processors could include one or more processors to control operation of the manipulator 56. The manipulator 56 may be in the form of a conventional robotic system or other conventional machining apparatus, and thus the components thereof shall not be described in detail.

The manipulator controller 54 determines the desired location to which the surgical tool 22 should be moved. Based on this determination, and information relating to the current location (e.g., pose) of the surgical tool 22, the manipulator controller 54 determines the extent to which each of the plurality of links 58 needs to be moved in order to reposition the surgical tool 22 from the current location to the desired location. The data regarding where the plurality of links 58 are to be positioned is forwarded to joint motor controllers (not shown) (e.g., one for controlling each motor) that control the active joints of the manipulator 56 to move the plurality of links 58 and thereby move the surgical tool 22 from the current location to the desired location.

Figure 3:
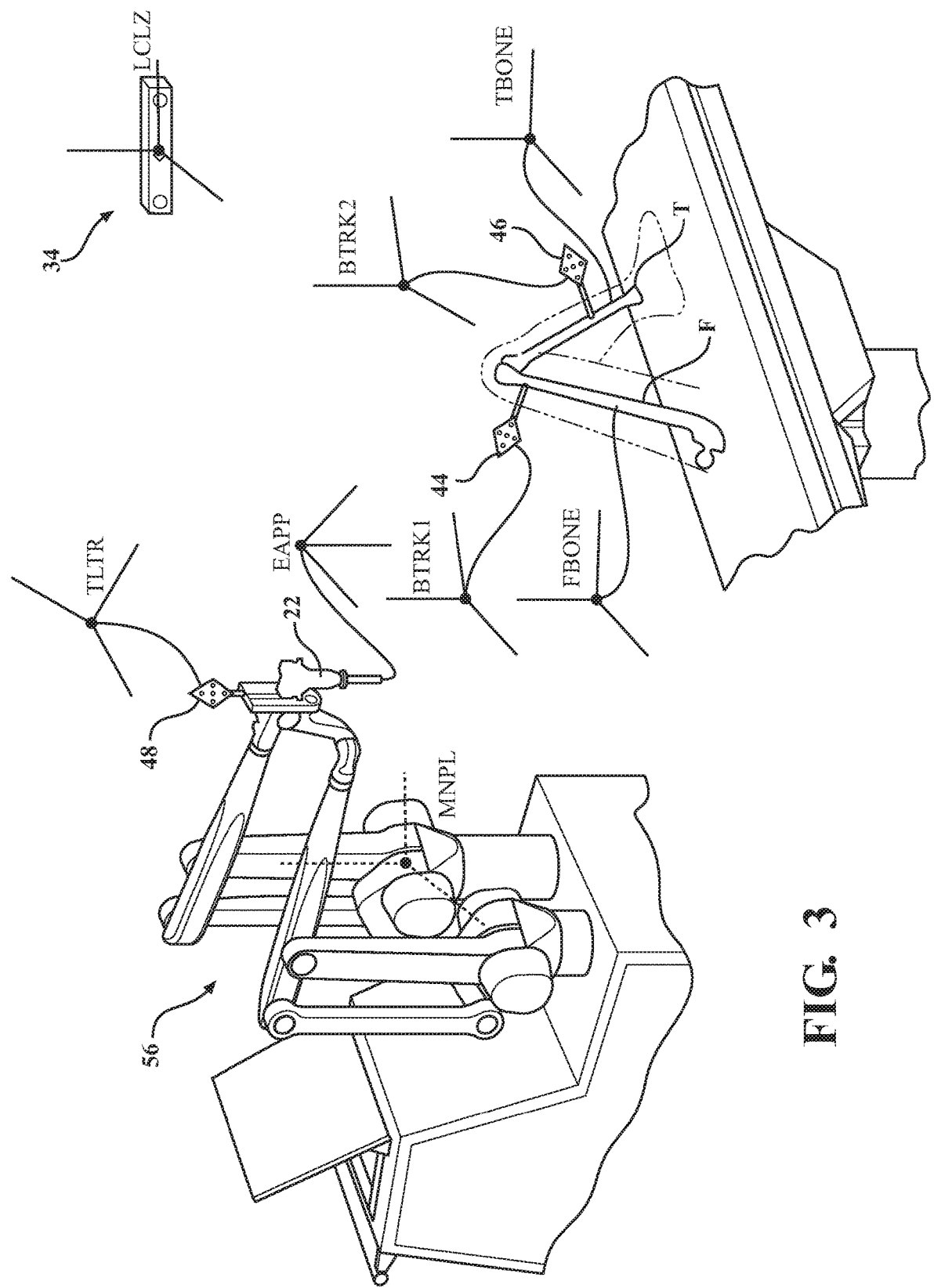
FIG. 3 is a perspective view of coordinate systems used by a surgical navigation system in conjunction with an alternative robotic surgical system.

Referring to FIG. 3, tracking of objects is generally conducted with reference to a localizer coordinate system LCLZ. The localizer coordinate system has an origin and an orientation (a set of x-, y-, and z-axes). During the procedure one goal is to keep the localizer coordinate system LCLZ in a known position. An accelerometer (not shown) mounted to the camera unit 36 may be used to track sudden or unexpected movement of the localizer coordinate system LCLZ, as may occur when the camera unit 36 is inadvertently bumped by surgical personnel.

Each tracker 44, 46, 48 and object being tracked also has its own coordinate system separate from localizer coordinate system LCLZ. Components of the navigation system 20 that have their own coordinate systems are the bone trackers 44 and 46, and the instrument tracker 48. These coordinate systems are represented as, respectively, bone tracker coordinate systems BTRK1 and BTRK2, and instrument tracker coordinate system TLTR.

Navigation system 20, through the localizer 34, monitors the positions of the femur F and tibia T of the patient by monitoring the position of bone trackers 44, 46 coupled to bone. The femur coordinate system is FBONE and the tibia coordinate system is TBONE, which are the coordinate systems of the bones to which the bone trackers 44, 46 are coupled.

Prior to the start of the procedure, pre-operative images of the femur F and tibia T are generated (or of other tissues in other embodiments). These images may be based on MRI scans, radiological scans or computed tomography (CT) scans of the patient's anatomy. These images are mapped to the femur coordinate system FBONE and tibia coordinate system TBONE using well known methods in the art. These images are fixed in the femur coordinate system FBONE and tibia coordinate system TBONE. As an alternative to taking pre-operative images, plans for treatment can be developed in the operating room (OR) from kinematic studies, bone tracing, and other methods.

During an initial phase of the procedure, the bone trackers 44, 46 are coupled to the bones of the patient. The pose (position and orientation) of coordinate systems FBONE and TBONE must be mapped to coordinate systems BTRK1 and BTRK2, respectively. Given the fixed relationship between the bones and their bone trackers 44, 46, positions and orientations of the femur F and tibia T in the femur coordinate system FBONE and tibia coordinate system TBONE must be transformed to the bone tracker coordinate systems BTRK1 and BTRK2 so the camera unit 36 is able to track the femur F and tibia T by tracking the bone trackers 44, 46. This pose-describing data are stored in memory integral with both manipulator controller 54 and navigation processor 52.

The working end of the surgical instrument 22 (also referred to as energy applicator distal end) has its own coordinate system EAPP. The origin of the coordinate system EAPP may represent a centroid of a surgical cutting bur, for example. The pose of coordinate system EAPP must be fixed to the pose of instrument tracker coordinate system TLTR before the procedure begins. Accordingly, the poses of these coordinate systems EAPP, TLTR relative to each other must be determined in the navigation computer 26. The pose-describing data are stored in memory integral with both manipulator controller 54 and navigation processor 52.

Referring back to FIG. 2, a localization engine 100 is a software module that may be included within the navigation system 20. Components of the localization engine 100 may execute on navigation processor 52. In some embodiments, however, the localization engine 100 may execute on the manipulator controller 54.

Localization engine 100 receives as inputs the optically-based signals from the camera controller 42 and, in some embodiments, the non-optically based signals from the tracker controller 62. Based on these signals, localization engine 100 determines the pose of the bone tracker coordinate systems BTRK1 and BTRK2 in the localizer coordinate system LCLZ. Based on the same signals received for the instrument tracker 48, the localization engine 100 determines the pose of the instrument tracker coordinate system TLTR in the localizer coordinate system LCLZ.

The localization engine 100 forwards the signals representative of the poses of trackers 44, 46, 48 to a coordinate transformer 102. Coordinate transformer 102 is a navigation system software module that runs on navigation processor 52. Coordinate transformer 102 references the data that defines the relationship between the pre-operative images of the patient and the bone trackers 44, 46. Coordinate transformer 102 also stores the data indicating the pose of the working end of the surgical instrument relative to the instrument tracker 48.

During the procedure, the coordinate transformer 102 receives the data indicating the relative poses of the trackers 44, 46, 48 to the localizer 34. Based on these data and the previously loaded data, the coordinate transformer 102 generates data indicating the relative position and orientation of the coordinate system EAPP, and the bone coordinate systems, FBONE and TBONE to the localizer coordinate system LCLZ.

As a result, coordinate transformer 102 generates data indicating the position and orientation of the working end of the surgical instrument 22 relative to the tissue (e.g., bone) against which the instrument working end is applied. Image signals representative of these data are forwarded to displays 28, 29 enabling the surgeon and staff to view this information. In certain embodiments, other signals representative of these data can be forwarded to the manipulator controller 54 to guide the manipulator 56 and corresponding movement of the surgical instrument 22.

In a similar manner, other trackers may be coupled to any other suitable object to be tracked within the operating room, and each object and associated tracker may be registered to the localizer coordinate system LCLZ as described above.

An improved method of registration, or calibration, eliminates the need to use a navigation pointer, referenced above, to touch objects to be tracked during calibration or registration. In accordance with the present disclosure, a method of locating a physical object in a target space, for registration or calibration, can include capturing one or more images at a first exposure, capturing one or more images at a second, different, exposure, estimating a tracker pose based on the first exposure images and correlating virtual object data to the estimated tracker pose in the second exposure images.

As used in the present disclosure, the term exposure refers to the amount of radiant energy absorbed at the optical sensor 40 within a discrete sensing cycle. Said differently, exposure is the amount of light, including infrared light, per unit area, or pixel, reaching the optical sensor 40, as determined by sensing time, lensing (if any), and luminance. With this understanding, the second exposure, as in the present disclosure, may be different from the first exposure in the length of time over which information is collected from the sensor. Alternatively, or in addition, the second exposure may be different from the first exposure in the level of luminance in the target space. The luminance may be varied by increasing or decreasing the power delivered to the LEDs emitting light into target space. This may include LEDs as markers on the trackers 44, 46, 48 or LEDs associated with the camera unit 36 (light from which is reflected by passive markers on the trackers 44, 46, 48).

The first and second exposures may differ by the length of time the optical sensors are actively sensing during the exposure. More specifically, the first exposure may be shorter in time than the second exposure, or vice versa. A short (e.g., first) exposure may limit the amount of radiant energy absorbed by the optical sensor 40 over a brief period of time. The resulting image after a short exposure may have low contrast between sensor pixels of small differences in energy magnitude at low energy levels. A short exposure image may be advantageous in identifying marker arrays on a tracker present in the target space. The markers, either reflecting or emitting radiation, will each present a high-intensity point on the image relative to the generally low-intensity surrounding area of the remaining target space. Therefore, the navigation computer may apply known pattern recognition algorithms to the short exposure image to discern the arrangement of tracker markers present in the target space.

During the surgical operation, other than during a calibration or registration phase, short exposure images, such as those described, may be used by the navigation computer to track movement of the objects in the target space over time. The short exposure images being limited to highlight and focus on the trackers themselves allow the rapid image acquisition and image processing necessary to rapidly update the virtual models of the tracked objects in order to keep the surgeon advised of the present positions and orientation with minimal or no latency.

A long (e.g., second) exposure allows a greater amount of radiant energy to be absorbed by the optical sensor 40 over a longer period of time relative to the short exposure. The resulting image will have greater contrast between pixels having even small differences in energy magnitude at lower energy levels. The surfaces of the tracked object may therefore be resolved in the long exposure image in a way not present at a short exposure. Therefore, a long exposure image may be advantageous in performing object recognition of the surgical tool or patient anatomy in the target space. Long exposure images may be used to create a model of the object or recognize the object relative to a pre-existing model. Where the object includes patient anatomy, the long exposure image may be used to generate surfaces of the patient for surface registration. One example form of object recognition includes stereoscopic measurement leading to a 3D point cloud of the surface.

In one embodiment of the present disclosure, the long exposure may be many times greater than the short exposure. For example, the short exposure may last between about 100-500 microseconds, whereas the long exposure may last between 10-50 milliseconds. In a further example, the short exposure is between 200-400 microseconds and the long exposure is between 20-40 milliseconds. In a still further example, the short exposure is 300 microseconds and the long exposure is 30 milliseconds. In a yet still further example, the long exposure may be greater than about 10 times as long as the short exposure.

The respective time duration of the short exposure and the long exposure may be selected in consideration of the system's capabilities and the environment in which it is deployed. As described above, where the optical sensors 40 are configured to sense light in the infrared or near-infrared spectrum, trackers may be employed that actively emit or reflect infrared light. In environments having a higher level of ambient infrared energy, or where the level of light actively emitted or reflected is lower relative to the ambient environment, the length of the exposures may be longer than in environments where the environment has less ambient energy or where the actively emitted or reflected energy is higher relative to the ambient environment. Other factors in the environment or in the system configuration impact the respective lengths of the short and long exposures. Throughout the specification, the terminology will be used to designate the short exposure as sufficient to detect the tracker markers and the long exposure as sufficient to detect, identify, or recognize aspects, characteristics, or geometry of the tracked object.

In order to minimize the effects of any transients in the system, the second exposure commences within a minimal interval following the conclusion of the first exposure. For example, the second exposure may commence about 100 milliseconds following the first exposure. In a further example, the second exposure may commence within about 100 nanoseconds following the first exposure. In a still further example, the second exposure may commence within about 100 microseconds following the first exposure. In a yet still further example, the interval between the long exposure and the short exposure may be shorter than the duration of the short exposure.

In some alternatives of the present disclosure, a series of multiple image acquisitions, each equivalent to a short exposure image may be stacked, or summed, in order to generate a single or multiple long exposure images. In such an embodiment, a series of short exposure images are collected and stacked in order to generate a long exposure image for processing to detect the object geometry. The short exposure image used in the disclosed method for detecting the tracker markers may be one of the stacked short exposure images, and particularly a middle image of the stacked sequence of images. Over the short duration of time that a sequence of short exposure images may be acquired, there may nonetheless be small movements of the tracker markers or tracked object. Using a middle image may minimize the effect these small movements may have on the calibration or registration of the tracker to the object.

In some embodiments, a single optical sensor 40 of camera unit 36 may be solely used to capture both short exposure images and long exposure images of the target space including the object to be tracked, with a tracker coupled thereto. By using a single optical sensor 40, with minimal latency between capturing long and short exposure images, the navigation computer 26 can relate the information in the two images quickly, with high precision and without requiring additional devices or predefined routines. In the embodiment shown, the camera unit 36 includes two optical sensors 40 arranged stereoscopically and separated by a separation distance, with both optical sensors 40 capturing short exposure images and long exposure images of the target space substantially simultaneously, and processing the images as described below to provide the navigation computer 26 with information to precisely locate the object in three-dimensional space. In this way, the present disclosure provides an improved method for calibrating or registering objects, including surgical tools and patient anatomy, for use with computer navigated surgical operations.

As described above, the navigation computer 26 stores virtual tracker data, including a representation of the marker array associated with the tracker. The navigation computer 26 estimates a tracker pose by relating one or more of the short exposure images with the virtual tracker data defining the marker arrangement using known image processing techniques that match locations of the markers in the one or more short exposure images with the virtual tracker data. A description of an exemplary technique for tracker estimation can be found in more detail, for example, in "Theory and Practice of Projective Rectification," by R. I. Hartley, International Journal of Computer Vision, Vol. 35, Issue 2, pp 115-127 (1999); and in "Multi View Geometry in Computer Vision, Second Edition," by R. Hartley and A. Zisserman, Cambridge University Press (Cambridge UK, 2000), the entireties of which are incorporated by reference. Likewise, the navigation computer 26 stores virtual object data as a representation of the object to be tracked. The navigation computer 26 correlates the virtual object data to the estimated tracker pose by recognizing the object in one or more long exposure images based on the virtual object data. A description of an exemplary technique for object recognition can be found in more detail, for example, in "Matching Shapes," by S. Belongie, J. Malik, and J. Puzicha, The 8th International Conference on Computer Vision, Vancouver, Canada, pp. 454-461 (2001), and in "Use of the Hough Transformation to Detect Lines and Curves in Pictures," by R. O. Duda and P. E. Hart, Communications of the ACM, Association for Computing Machinery, Vo. 15, pp. 11-15 (Janvier 1972), the entireties of which are incorporated by reference.

The processes set forth herein may be described using terms of singular occurrence, e.g. acquiring an image. One of ordinary skill appreciates that the operations described in acquiring images and processing those images all occur over very brief periods of time. The navigation system 20 may be configured to operate such that this improved process of calibration or registration occurs many times in rapid succession wherein the successive process results are combined together to achieved a more precise calibration or registration. For example, if coordinate position values or orientation vary slightly across successive instances of imaging and processing, the ultimate calibration or registration may be an average of the individual analyses.

In addition, the disclosed process is described above as acquiring images using first and second optical sensors generally directed toward a stationary object. In executing multiple sequences of image acquisition and processing, the registration or calibration accuracy and precision may be improved when the relative perspective between the optical sensors and the object is varied during the registration or calibration process. For example, during a registration or calibration process, a patient's anatomy may be moved through a range of motion (such as bending or extending a leg at the knee joint), or a surgical tool may be rotated so that different sides of the tool are visible to the localizer, or the tool may be moved through different distances away from the localizer. Providing multiple views of the tracked object allows the system to refine the link between the tracker markers and the virtual data representing the object. For example, the system may build a more complete 360° model of the object, if building the object through intraoperative imaging.

Furthermore, while described as an initial step preceding a surgical operation, a surgeon or other operator may initiate a recalibration or repeated registration if an error is noticed, if the surgery is interrupted, or if it is believed that the calibration or registration has otherwise been adversely impacted during the course of the operation. Therefore, the improved method as disclosed herein may be selectively performed at various times throughout the surgical operation. The disclosed method eliminates the need for additional equipment, such as a navigation pointer, and the need to execute a prescribed routine for registration or calibration and therefore is particularly advantageous to minimize any interruption to the surgical operation due to repeated calibration or registration.

Specific use cases of the above-disclosed improved method of calibration and registration are provided with specific reference to FIGS. 4-6A & B; and FIGS. 7-9A & B.

Figure 4:
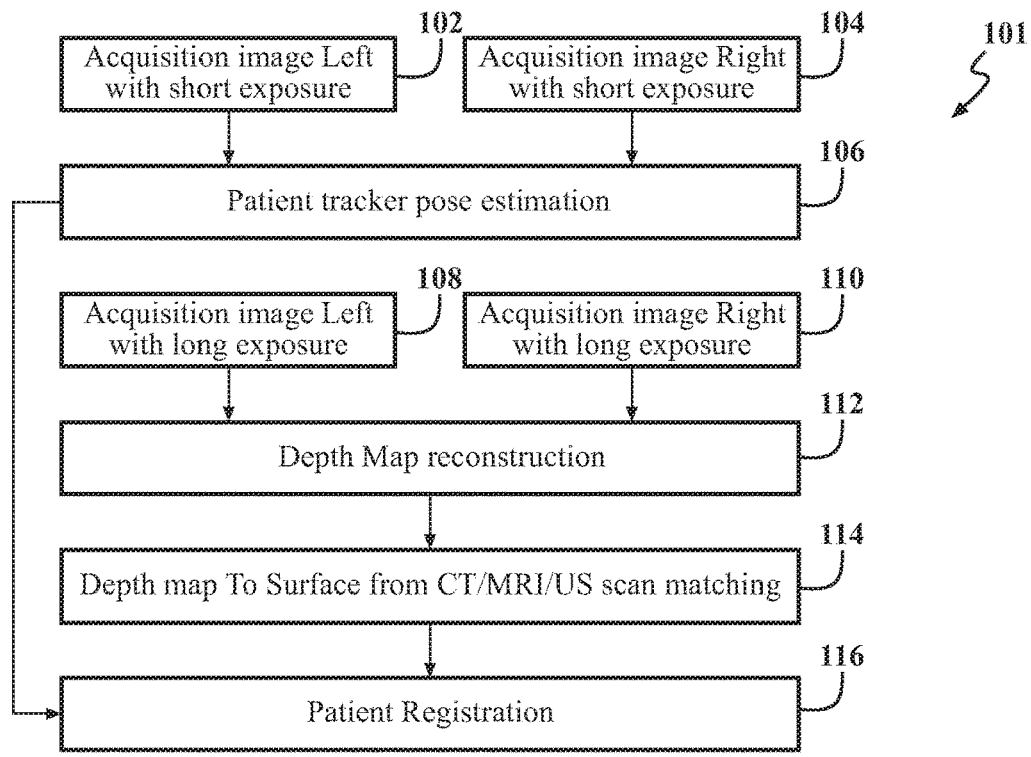
FIG. 4 is a flow diagram of a first embodiment of a method for locating a physical object in a target space according to the present disclosure.

Referring now to FIG. 4, a method 101 of registering a patient anatomy according to the present disclosure is illustrated. In the first steps 102, 104 of the method 101, short exposure images are acquired by the left optical sensor 40 of the camera unit 36 and by the right optical sensor 40 of the camera unit 36. The short exposure is preferably 300 microseconds.

For step 106, the short exposure images are communicated by the camera controller 42 to the navigation computer 26. The navigation computer 26 determines a pattern of tracker markers in each of the short exposure images, using known techniques. A description of this technique for pattern recognition can be found, for example, in "Closed-form Solution of Absolute Orientation Using Unit Quaternions," by B. K. P. Horn, Journal of the Optical Society of America A, Vol. 4, Issue 4, pp. 629-642 (April 1987), the entirety of which is incorporated by reference. The navigation computer 26 retrieves the virtual tracker data, for example, by querying a database of virtual tracker data stored in the memory of the navigation computer 26. The navigation computer 26 relates the pattern of tracker markers to the virtual tracker data for each short exposure image to estimate a pose of the tracker in the target space.

In steps 108, 110, long exposure images are acquired by the left optical sensor 40 of the camera unit 36 and by the right optical sensor 40 of the camera unit 36. The long exposure is preferably 10 times longer than the short exposure, or about 30 milliseconds. The long exposure commences within about 300 microseconds or less following the short exposure. Although presented in an order such that the processing of the short-exposure images to estimate a tracker pose occurs prior to the capturing of the long exposure images, this is not intended to limit the scope of the present disclosure. Rather, one of ordinary skill appreciates that the short exposure images may be acquired, followed by the acquisition of the long exposure images, which is thereafter followed by the processing of the short exposure images to estimate a tracker pose.

Following the acquisition of the long exposure images, at step 112, the long exposure images are communicated by the camera controller 42 to the navigation computer 26. The navigation computer 26 retrieves virtual object data representing the object to be tracked. The virtual object data comprises the patient anatomy captured as one or more preoperative images to generate a 3D model. The navigation computer 26 relates the long exposure images to the virtual object data, and in the embodiment illustrated in FIG. 4, constructs a depth map for matching similar features between the two stereo images using, for example, block matching methods so that the depth map obtained is then geometrically aligned with the 3D model of the virtual object data at step 114. A description of this technique can be found described in more detail, for example in "A Taxonomy and Evaluation of Dense Two-Frame Stereo Correspondence Algorithms," by D. Scharstein and R. Szeliski, International Journal of Computer Vision, Vol. 47, pp. 1-3 and 7-42 (April 2002), the entirety of which is incorporated by reference. Additional descriptions can be found, for example, in "Advances in Computational Stereo," by M. Z. Brown, D. Burschka, and G. D. Hager, IEEE Transactions on Pattern Analysis and Machine Intelligence, Vol. 25, Issue 8, pp. 993-1008 (August 2003); and "Stereo Processing by Semiglobal Matching and Mutual Information," by H. Hirschmuller, IEEE Transactions on Pattern Analysis and Machine Intelligence, Vol. 30, Issue 2, pp. 328-341 (February 2008), the entireties of which are incorporated by reference.

Utilizing the known relationship between the rigidly mounted left and right optical sensors 40 of camera unit 36, and the correspondence between the short and long exposures taken by each of the left and right optical sensors 40, the navigation computer 26 completes the registration of the patient anatomy.

Figure 5:
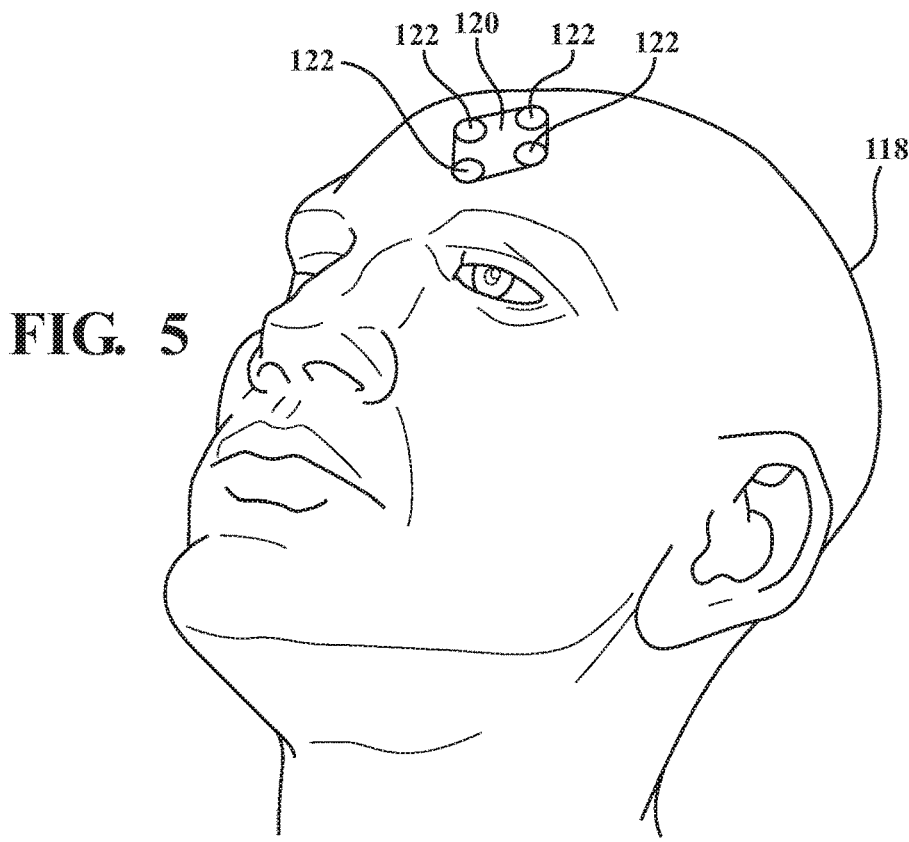
FIG. 5 is an example of a patient anatomy including a tracker.
Figure 6A:
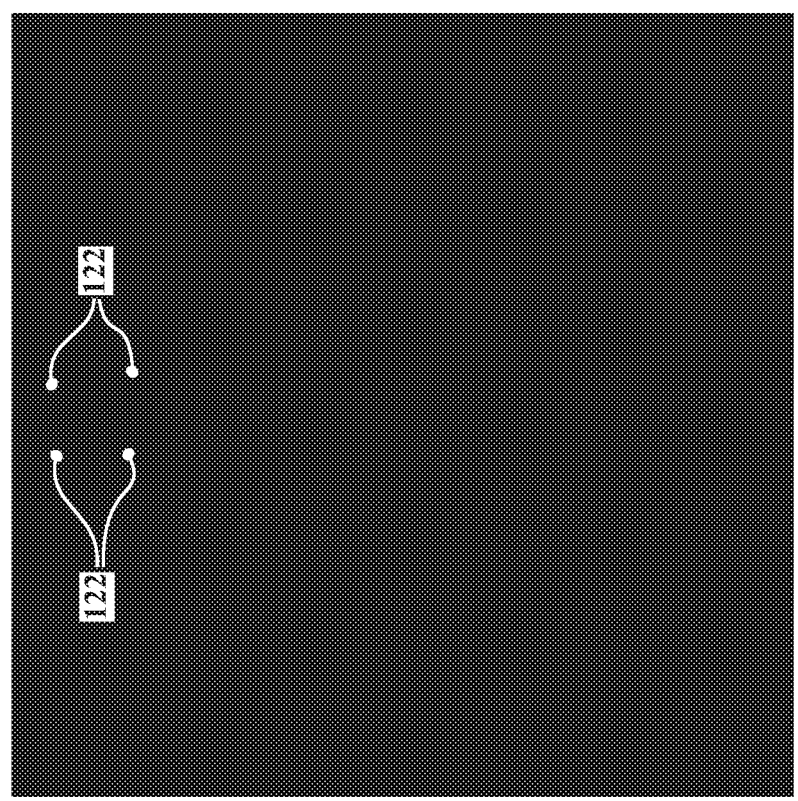
FIG. 6A is a first example of an image of the target space taken at a first exposure.
Figure 6B:
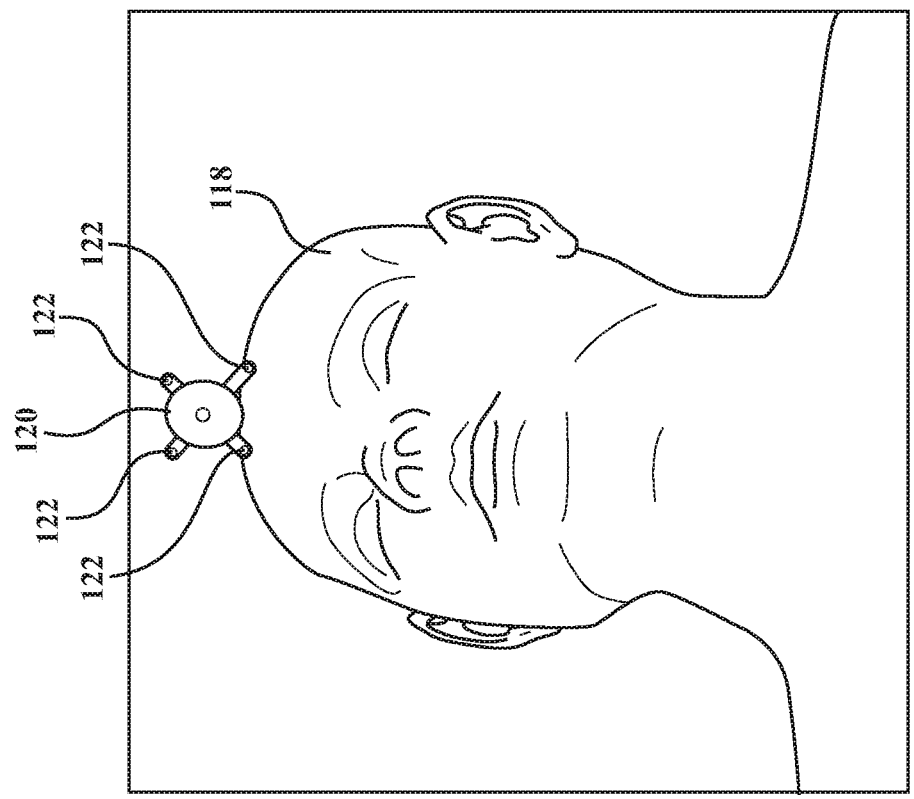
FIG. 6B is a first example of an image of the target space taken at a second exposure.

FIG. 5 illustrates an exemplary patient anatomy for use with the improved method of the present disclosure. A patient 118 is shown, for example, in preparation for neurosurgery. A tracker 120 is affixed to the patient anatomy. The tracker 120 includes an array of four fiducial markers 122. FIGS. 6A and 6B illustrates exemplary short exposure and long exposure images, respectively, acquired according to the present disclosure. In FIG. 6A, the short exposure limits the amount of energy absorbed by the optical sensor 40. The higher-intensity markers 122 are visible in the image in a high contrast with the background whereas the details of the surrounding background are indistinguishable. In contrast, as shown in FIG. 6B, the long exposure allows additional energy to be absorbed at the optical sensor 40 to create contrast in the background and surroundings adjacent to the tracker 120 mounted on the patient anatomy. In this way, the navigational computer 26 uses the short exposure image to recognize the tracker marker arrangement to relate to the virtual tracker data. Likewise, the navigational computer 26 uses the long exposure image to recognize the patient anatomy to relate to the virtual object data.

Figure 7:
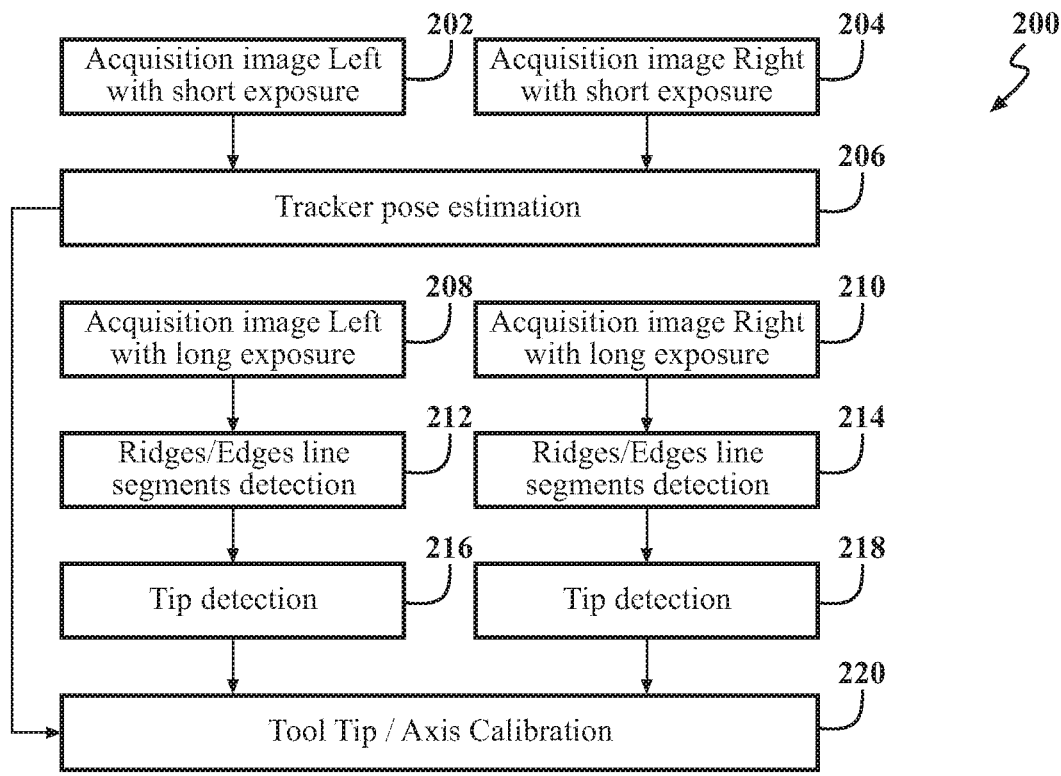
FIG. 7 is a flow diagram of a second embodiment of a method for locating a physical object in a target space according to the present disclosure.

Referring now to FIG. 7, a method 200 of calibrating a surgical tool according to the present disclosure is illustrated. In the first steps 202, 204 of the method 200, short exposure images are acquired by the left optical sensor 40 of the camera unit 36 and by the right optical sensor 40 of the camera unit 36. The short exposure is preferably 300 microseconds.

For step 206 the short exposure images are communicated by the camera controller 42 to the navigation computer 26.

The navigation computer 26 determines a pattern of tracker markers in each of the short exposure images. The navigation computer 26 retrieves the virtual tracker data, for example, by querying a database of virtual tracker data stored in memory of the navigation computer 26. The navigation computer 26 relates the pattern of tracker markers to the virtual tracker data for each short exposure image to estimate a pose of the tracker in the target space.

In steps 208, 210, long exposure images are acquired by the left optical sensor 40 of the camera unit 36 and by the right optical sensor 40 of the camera unit 36. The long exposure is preferably 10 times longer than the short exposure, or about 30 milliseconds. The long exposure commences within about 300 microseconds or less following the short exposure. Although presented in an order such that the processing of the short-exposure images to estimate a tracker pose occurs prior to the capturing of the long exposure images, this is not intended to limit the scope of the present disclosure. Rather, one of ordinary skill appreciates that the short exposure images may be acquired, followed by the acquisition of the long exposure images, which is thereafter followed by the processing of the images.

Following the acquisition of the long exposure images, at step 212, 214, the long exposure images are communicated by the camera controller 42 to the navigation computer 26. The navigation computer 26 retrieves virtual object data representing the object to be tracked. The virtual object data corresponds to the tool geometry and is used to generate a 3D model of the tool as a virtual object. The navigation computer 26 relates the long exposure images to the virtual object data, and in the embodiment illustrated in FIG. 7, applies a detection algorithm to recognize ridges and edges to discern the shape of the surgical tool in the two stereo images to geometrically align with the 3D model of the virtual object data at step 216, 218. A description of this technique can be found in more detail, for example, in the publication "Use of the Hough Transformation to Detect Lines and Curves in Pictures," by R. O. Duda and P. E. Hart, Communications of the ACM, Association for Computing Machinery, Vo. 15, pp. 11-15 (Janvier 1972), the entirety of which is incorporated by reference. The result of the processing of the long exposure images through steps 212, 214, 216, and 218, is that the position and orientation of the tool tip is known in the reference coordinate system.

As step 220, utilizing the known relationship between the rigidly mounted left and right optical sensors 40 of camera unit 36, and the correspondence between the short and long exposures taken by each of the left and right optical sensors 40, allows the navigation computer 26 to complete the calibration of the surgical tool. The rigid relationship between the tracker and the tool geometry is captured and reflected in the virtual environment of the navigation computer 26, thereby providing tracking of the tool, and specifically the tool tip, by detecting and tracking the movement of the tracker's markers.

Figure 8:
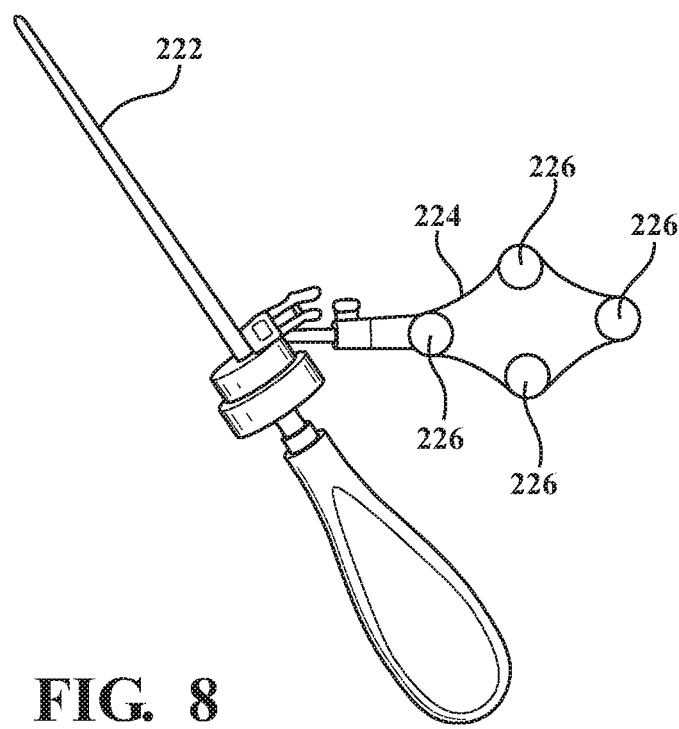
FIG. 8 is an illustration of an example surgical tool including a tracker.
Figure 9B:
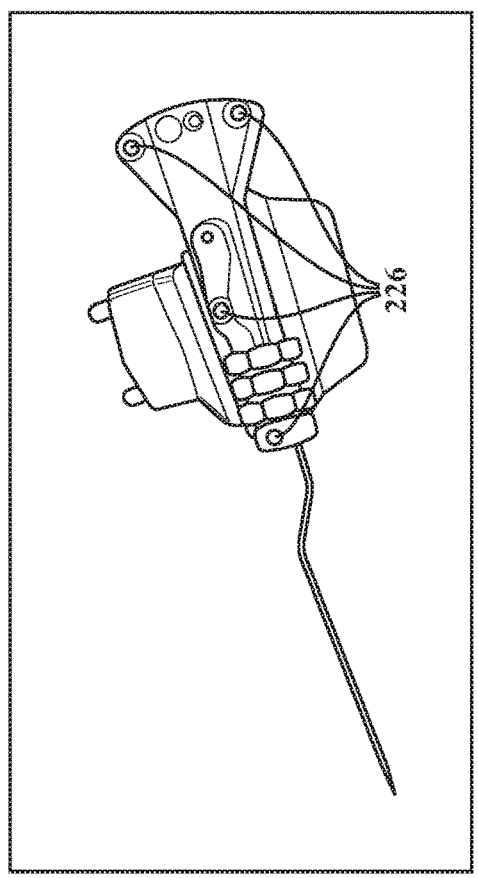
FIG. 9B is a second example of an image of the target space taken at a second exposure.
Figure 9A:
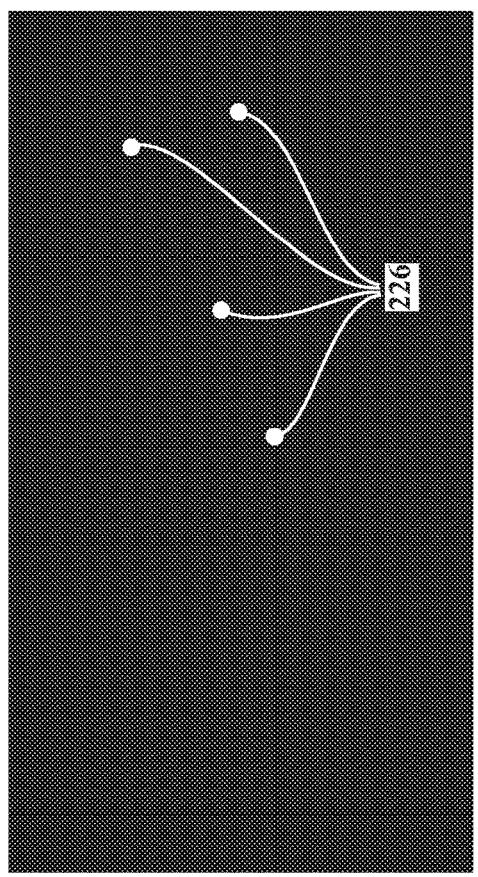
FIG. 9A is a second example of an image of the target space taken at a first exposure.

FIG. 8 illustrates an exemplary surgical tool 222 for use with the improved method of the present disclosure. A tool 222 is shown, for example, in preparation for use during an operation. A tracker 224 is affixed to the tool. The tracker 224 includes an array of four fiducial markers 226. FIGS. 9A and 9B illustrates exemplary short exposure and long exposure images, respectively, acquired according to the present disclosure. In FIG. 9A, the short exposure limits the amount of energy absorbed by the optical sensor 40. The higher-intensity markers 226 are visible in the image in a high contrast with the background whereas the details of the surrounding background are indistinguishable. In contrast, as shown in FIG. 9B, the long exposure allows additional energy to be absorbed at the optical sensor 40 to create contrast in the background and surroundings adjacent to the tracker 224 incorporated into the tool 222. In this way, the navigational computer 26 uses the short exposure image to recognize the tracker marker arrangement to relate to the virtual tracker data. Likewise, the navigational computer 26 uses the long exposure image to recognize the tool to relate to the virtual object data. Accordingly, for example, a tip of the tool can be calibrated, i.e., its position determined with respect to the pose of the tracker 224 for purposes of tracking the tip during the surgical procedure.

In an alternative embodiment to the above-described methods, the image acquisition steps are completed prior to processing the data contained in the acquired images. The short exposure images, acquired at steps 102, 104 of FIG. 4 or 202, 204 of FIG. 7, may be combined together with the long exposure images, acquired at steps 108, 110 of FIG. 4 or 208, 210 of FIG. 7. The tracker pose estimation step (106 of FIG. 4, or 206 of FIG. 7) and the object recognition steps (112-114 of FIG. 4 or 208-218 of FIG. 7) are performed on the combined image. Threshold filters may be applied to the combined images to filter image information and facilitate the separate processing of tracker data from object data. A post-acquisition image processing method is advantageous, for example, where an HDR camera is used as the optical sensor 40 in the camera unit 36 to automatically output single, combined HDR images.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method of registering a physical object to a tracker in a target space for location tracking, the physical object having a geometry represented by virtual object data, the tracker coupled to the physical object for movement therewith, the tracker having a marker array and the marker array having a marker arrangement represented by virtual tracker data, the method comprising:
    capturing one or more first exposure images of the target space containing the physical object and the tracker at a first exposure with a first of at least one camera;
    capturing one or more second exposure images of the target space containing the physical object and the tracker at a second exposure with the first of the at least one camera, wherein the first exposure is shorter in time than the second exposure;
    estimating a tracker pose based on the one or more first exposure images by relating the marker arrangement recognized in the one or more first exposure images with the virtual tracker data representing the marker arrangement;
    recognizing a position of the physical object in the one or more second exposure images based on the virtual object data; and
    correlating the position of the physical object recognized in the one or more second exposure images to the estimated tracker pose to define a registration between the tracker and the physical object.

2. The method of claim 1, comprising capturing one or more first exposure images of the target space with a second of the at least one camera.

3. The method of claim 2, wherein the first of the at least one camera and the second of the at least one camera are rigidly mounted to a common support structure and separated by a separation distance.

4. The method of claim 3, wherein the separation distance is selected from among: greater than six inches, greater than eight inches, greater than twelve inches, or greater than twenty-four inches.

5. The method of claim 2, wherein the second of the at least one camera comprises an infrared imaging device.

6. The method of claim 1, comprising capturing one or more second exposure images of the target space with a second of the at least one camera.

7. The method of claim 1, further comprising generating virtual object data representing the geometry based on the one or more second exposure images.

8. The method of claim 1, further comprising retrieving virtual object data representing the geometry from a database, the virtual object data based on preoperative imaging of the physical object.

9. The method of claim 1, further comprising generating virtual tracker data representing the marker arrangement based on the one or more first exposure images.

10. The method of claim 1, further comprising retrieving virtual tracker data representing the marker arrangement from a database; the virtual tracker data based on a predefined marker arrangement.

11. The method of claim 1, wherein the first exposure has a duration in a range of 100 to 500 microseconds.

12. The method of claim 1, wherein the first exposure has a duration in a range of 200 to 400 microseconds.

13. The method of claim 1, wherein the first exposure has a first duration and the second exposure has a second duration, and wherein the second duration is at least 10 times the first duration.

14. The method of claim 1, wherein the second exposure has a duration in a range of 10 to 50 milliseconds.

15. The method of claim 1, wherein the second exposure has a duration in a range of 20 to 40 milliseconds.

16. The method of claim 1, wherein the step of capturing the one or more second exposure images commences within an interval following the step of capturing the first exposure images at the first exposure, and wherein the interval is less than 300 microseconds.

17. The method of claim 1, wherein the physical object comprises a patient's anatomy, the method further comprising the steps of capturing preoperative images of the patient's anatomy; and generating virtual object data from the preoperative images.

18. The method of claim 1, wherein the physical object comprises a surgical tool, the method further comprising the steps of querying a database of surgical tool models; and
retrieving virtual object data based on querying the database of surgical tool models.

19. The method of claim 1, further comprising the step of querying a database of virtual tracker data.

20. The method of claim 1, wherein the first of the at least one camera comprises an infrared imaging device.

21. The method of claim 1, further comprising the step of emitting infrared light onto the target space with an infrared emitter.

22. A system for registering a physical object to a tracker in a target space for location tracking, the physical object having a geometry represented by virtual object data, the tracker coupled to the physical object for movement therewith, the tracker having a marker array and the marker array having a marker arrangement defined by virtual tracker data, the system comprising:
a first camera operable to capture first exposure images of the target space at a first exposure and second exposure images of the target space at a second exposure, wherein the first exposure is shorter in time than the second exposure;
a control and processing subsystem in electronic communication with the first camera; the control and processing system comprising:
a memory device operable to store virtual object data, and virtual tracker data;
the control and processing subsystem comprising instructions that when executed cause the system to:
capture one or more first exposure images of the target space containing the physical object and the tracker at the first exposure with the first camera;
capture one or more second exposure images of the target space containing the physical object and the tracker at the second exposure with the first camera;
estimate a tracker pose based on the one or more first exposure images by relating the marker arrangement recognized in the one or more first exposure images with the virtual tracker data defining the marker arrangement;
recognize a position of the physical object in the one or more second exposure images based on the virtual object data; and
correlate the position of the physical object recognized in the one or more second exposure images to the estimated tracker pose to define a registration between the tracker and the physical object.

23. A method of registering a physical object to a tracker in a target space for location tracking, the physical object having a geometry represented by virtual object data, the tracker coupled to the physical object for movement therewith, the tracker having a marker array and the marker array having a marker arrangement represented by virtual tracker data, the method comprising:
capturing one or more first exposure images of the target space containing the physical object and the tracker at a first exposure with a first of at least one camera;
capturing one or more second exposure images of the target space containing the physical object and the tracker at a second exposure with the first of the at least one camera, wherein the first exposure is lower in illumination than the second exposure;
estimating a tracker pose based on the one or more first exposure images by relating the marker arrangement recognized in the one or more first exposure images with the virtual tracker data representing the marker arrangement;
recognizing a position of the physical object in the one or more second exposure images based on the virtual object data; and
correlating the position of the physical object recognized in the one or more second exposure images to the estimated tracker pose to define a registration between the tracker and the physical object.

24. A system for registering a physical object to a tracker in a target space for location tracking, the physical object having a geometry represented by virtual object data, the tracker coupled to the physical object for movement therewith, the tracker having a marker array and the marker array having a marker arrangement defined by virtual tracker data, the system comprising:
- a first camera operable to capture first exposure images of the target space at a first exposure and second exposure images of the target space at a second exposure, wherein the first exposure is lower in illumination than the second exposure;
- a control and processing subsystem in electronic communication with the first camera; the control and processing system comprising:
  - a memory device operable to store virtual object data, and virtual tracker data;
  - the control and processing subsystem comprising instructions that when executed cause the system to:
    - capture one or more first exposure images of the target space containing the physical object and the tracker at the first exposure with the first camera;
    - capture one or more second exposure images of the target space containing the physical object and the tracker at the second exposure with the first camera;
    - estimate a tracker pose based on the one or more first exposure images by relating the marker arrangement recognized in the one or more first exposure images with the virtual tracker data defining the marker arrangement;
    - recognize a position of the physical object in the one or more second exposure images based on the virtual object data; and
    - correlate the position of the physical object recognized in the one or more second exposure images to the estimated tracker pose to define a registration between the tracker and the physical object.

25. A method of registering a physical object to a tracker in a target space for location tracking, the physical object having a geometry represented by virtual object data, the tracker coupled to the physical object for movement therewith, the tracker having a marker array and the marker array having a marker arrangement represented by virtual tracker data, the method comprising:
- capturing one or more first exposure images of the target space containing the physical object and the tracker at a first exposure with a first of at least one camera;
- capturing one or more second exposure images of the target space containing the physical object and the tracker at a second exposure with the first of the at least one camera, wherein the first exposure is longer in time than the second exposure;
- estimating a tracker pose based on the one or more first exposure images by relating the marker arrangement recognized in the one or more first exposure images with the virtual tracker data representing the marker arrangement;
- recognizing a position of the physical object in the one or more second exposure images based on the virtual object data; and
- correlating the position of the physical object recognized in the one or more second exposure images to the estimated tracker pose to define a registration between the tracker and the physical object.

26. A system for registering a physical object to a tracker in a target space for location tracking, the physical object having a geometry represented by virtual object data, the tracker coupled to the physical object for movement therewith, the tracker having a marker array and the marker array having a marker arrangement defined by virtual tracker data, the system comprising:
- a first camera operable to capture first exposure images of the target space at a first exposure and second exposure images of the target space at a second exposure, wherein the first exposure is longer in time than the second exposure;
- a control and processing subsystem in electronic communication with the first camera; the control and processing system comprising:
  - a memory device operable to store virtual object data, and virtual tracker data;
  - the control and processing subsystem comprising instructions that when executed cause the system to:
    - capture one or more first exposure images of the target space containing the physical object and the tracker at the first exposure with the first camera;
    - capture one or more second exposure images of the target space containing the physical object and the tracker at the second exposure with the first camera;
    - estimate a tracker pose based on the one or more first exposure images by relating the marker arrangement recognized in the one or more first exposure images with the virtual tracker data defining the marker arrangement;
    - recognize a position of the physical object in the one or more second exposure images based on the virtual object data; and
    - correlate the position of the physical object recognized in the one or more second exposure images to the estimated tracker pose to define a registration between the tracker and the physical object.

27. A method of registering a physical object to a tracker in a target space for location tracking, the physical object having a geometry represented by virtual object data, the tracker coupled to the physical object for movement therewith, the tracker having a marker array and the marker array having a marker arrangement represented by virtual tracker data, the method comprising:
- capturing one or more first exposure images of the target space containing the physical object and the tracker at a first exposure with a first of at least one camera;
- capturing one or more second exposure images of the target space containing the physical object and the tracker at a second exposure with the first of the at least one camera, wherein the first exposure is higher in illumination than the second exposure;
- estimating a tracker pose based on the one or more first exposure images by relating the marker arrangement recognized in the one or more first exposure images with the virtual tracker data representing the marker arrangement;
- recognizing a position of the physical object in the one or more second exposure images based on the virtual object data; and
- correlating the position of the physical object recognized in the one or more second exposure images to the estimated tracker pose to define a registration between the tracker and the physical object.

28. A system for registering a physical object to a tracker in a target space for location tracking, the physical object having a geometry represented by virtual object data, the tracker coupled to the physical object for movement therewith, the tracker having a marker array and the marker array having a marker arrangement defined by virtual tracker data, the system comprising:
- a first camera operable to capture first exposure images of the target space at a first exposure and second exposure images of the target space at a second exposure, wherein the first exposure is higher in illumination than the second exposure;
- a control and processing subsystem in electronic communication with the first camera; the control and processing system comprising:
  - a memory device operable to store virtual object data, and virtual tracker data;
  - the control and processing subsystem comprising instructions that when executed cause the system to:
    - capture one or more first exposure images of the target space containing the physical object and the tracker at the first exposure with the first camera;
    - capture one or more second exposure images of the target space containing the physical object and the tracker at the second exposure with the first camera;
    - estimate a tracker pose based on the one or more first exposure images by relating the marker arrangement recognized in the one or more first exposure images with the virtual tracker data defining the marker arrangement;
    - recognize a position of the physical object in the one or more second exposure images based on the virtual object data; and
    - correlate the position of the physical object recognized in the one or more second exposure images to the estimated tracker pose to define a registration between the tracker and the physical object.

* * * * *